US011623092B2

(12) United States Patent
Peyman et al.

(10) Patent No.: US 11,623,092 B2
(45) Date of Patent: Apr. 11, 2023

(54) IMPLANTABLE NEUROSTIMULATOR

(71) Applicants: Nazmi Peyman, Richmond, VA (US); Edmond Zahedi, Burnaby (CA)

(72) Inventors: Nazmi Peyman, Richmond, VA (US); Edmond Zahedi, Burnaby (CA)

(*) Notice: Subject to any disclaimer, the term of this patent is extended or adjusted under 35 U.S.C. 154(b) by 0 days.

(21) Appl. No.: 17/392,237

(22) Filed: Aug. 2, 2021

(65) Prior Publication Data
US 2022/0047867 A1   Feb. 17, 2022

Related U.S. Application Data

(60) Provisional application No. 63/060,098, filed on Aug. 2, 2020.

(51) Int. Cl.
*A61N 1/36* (2006.01)

(52) U.S. Cl.
CPC ..... *A61N 1/36071* (2013.01); *A61N 1/36062* (2017.08); *A61N 1/36178* (2013.01)

(58) Field of Classification Search
CPC ............ A61N 1/36071; A61N 1/36062; A61N 1/36178; A61N 1/36139; A61B 5/242; A61B 5/40; A61B 5/4836
See application file for complete search history.

(56) References Cited

U.S. PATENT DOCUMENTS

| 2016/0310732 A1* | 10/2016 | Beck | A61N 2/06 |
| 2016/0374579 A1* | 12/2016 | Chien | A61B 5/6877 |
| | | | 600/409 |
| 2019/0223777 A1* | 7/2019 | Dubhashi | A61B 5/24 |

* cited by examiner

*Primary Examiner* — Paula J Stice
(74) *Attorney, Agent, or Firm* — Barry Choobin; Patent 360

(57) ABSTRACT

A system for stimulating a tissues to obtain therapeutic effects, such as pain relief. The system can include stimulating leads that are operably coupled to a control unit. The control unit can include processors for generating desired waveform pattern of electrical pulses. The system can further include magnetic sensors to measure the magnetic fields generated by action potentials in the excited tissue and using the measured magnetic field to optimize the neurostimulation pattern.

15 Claims, 11 Drawing Sheets

Waveform 1

Waveform 2

Waveform 3

Waveform 4

IMPLANTABLE NEUROSTIMULATOR

CROSS-REFERENCE TO RELATED APPLICATIONS

This application claims priority to the U.S. provisional patent application Ser. No. 63/060,098, filed on Aug. 2, 2020, which is incorporated herein by reference in its entirety.

FIELD OF INVENTION

The present invention relates to a neurostimulator, and more particularly, disclosed is a system and method for neurostimulation that can modify the neurostimulation based on feedback.

BACKGROUND

Electrical neurostimulation has been used since the 1960s in treating a variety of chronic pain syndromes. This works by targeted delivery of electrical energy to specific areas of the nervous systems. For example, in spinal cord stimulation (SCS), stimulation leads are implanted in the posterior epidural space as the stimulation site and leads are then connected to a pulse generator implanted subcutaneously. Electrical pulses can be delivered from the pulse generator to the leads to stimulate the tissue for the desired therapy. Deep Brain Stimulation and Peripheral Nerve Stimulation (PNS) have been widely used as a therapeutic modality in a variety of chronic pains. Functional Electrical Stimulation (FES) has been investigated for restoring functionality to paralyzed extremities.

During a stimulation pulse, negative charges flow from a negatively charged electrode (cathode) to a positively charged electrode (anode). The mechanism of action of nerve stimulation is thought to be through Melzack and Wall's "Gate Theory". Large fiber afferents are activated during stimulation within the usage range and can subsequently 'close the gate' to painful stimuli.

Generally, the amount of electrical energy delivered to the tissues is controlled by either keeping the voltage or the current constant. Numerous studies comparing these two modalities lead to an overall estimation of the success in spinal cord stimulation (as an example) in treating chronic pain syndrome to between 40% and 60%. Neuromodulation does not work for all patients with all types of pain. Depending upon the scientific studies, 50 to 70% of patients suitable for neuromodulation may experience a 50% reduction in their reported pain at follow-up. This would mean that 30-50% of patients will be experiencing more than 50% of their initial pain with the present spinal cord stimulation and neuromodulation technologies.

Existing and emerging neuromodulation treatments also include other applications in medication-resistant epilepsy, bladder and bowel control, improvement of sensory deficits, such as hearing (cochlear implants and auditory brainstem implants) and vision (retinal implants). Neuromodulation therapy has also been investigated in Alzheimer's disease, depression, and in recovery from stroke.

Research has shown that the limited success of existing systems may be attributable to the following factors: (1) imperfect matching of the type of electrical pulse to the ever-changing physiological conditions of a patient, (2) gradual modification of the electrode-tissue interface rendering the stimulation less effective over time, (3) accommodation of the nerves to the electrical stimulation, as the body becomes increasingly tolerant to the treatment. The above factors imply a less than ideal satisfaction rate among patients and necessitate reprogramming of the implanted device, which is a time-consuming and error-prone task.

To compensate for the shortcomings related to the aforesaid items namely (1) imperfect matching of the type of electrical pulse to the ever-changing physiological conditions of a patient, and (2) gradual modification of the electrode-tissue interface rendering the stimulation less effective over time, conventional systems consist of constant voltage and constant current stimulation. These techniques control the amount of delivered energy, not the end result.

On the other hand, increasing the energy delivered per pulse is not an acceptable solution as it may cause discomfort due to stimulation to other nerve structures not related to pain-related pathways causing side-effects, potentially causing tissue/nerve damage which may lead to scar formation at the electrode-tissue interface, causing more complications.

Therefore, a desire is there for an improved method of neurostimulation based on more direct feedback from the stimulated tissues that is devoid of the drawbacks of the known programmable neurostimulators and can provide the desired stimulation effect in the tissues of interest.

SUMMARY OF THE INVENTION

The following presents a simplified summary of one or more embodiments of the present invention in order to provide a basic understanding of such embodiments. This summary is not an extensive overview of all contemplated embodiments and is intended to neither identify key or critical elements of all embodiments nor delineate the scope of any or all embodiments. Its sole purpose is to present some concepts of one or more embodiments in a simplified form as a prelude to the more detailed description that is presented later.

The principal object of the present invention is therefore directed to a system and method for neurostimulation that is based on feedback to control the type of neurostimulation.

It is still another object of the present invention that the system and method can increase the success rate of therapy.

In one aspect, disclosed is a system and method for neurostimulation as a therapeutic modality for pain relief and other therapeutic uses. The disclosed system and method can provide for monitoring the magnetic field strength and using that parameter to regulate the amount of electrical energy delivered and waveform of the electrical pulses to the central and/or peripheral nervous system tissues.

In one aspect, the type of electrical stimulus can be determined by the feedback recorded from magnetic sensors. The passage of currents through the excited tissues generates a magnetic field, which can be picked up by the magnetic sensors to obtain a signal of interest. Based on the signal of interest, the neurostimulation pattern including the waveform pattern, energy of pulses, average power, peak values, current/voltage and like parameters known to a skilled person related to neurostimulation can be modified to enhance the neurostimulation effect.

In one aspect, disclosed is a system for neurostimulation, the system can include: one or more stimulating leads configured to transmit a neurostimulation pattern to a tissue, a control unit operably coupled to the one or more stimulating leads; and one or more magnetic sensors operably coupled to the control unit and configured to measure the magnetic fields generated by action potentials in an excited tissue in response to a neurostimulation pattern. The control unit can excite tissues with a first neurostimulation pattern, receive a first magnetic signal corresponding to the first neurostimulation pattern from the one or more magnetic sensors, and apply machine a learning algorithm to the first neurostimulation pattern and the first magnetic signal to generate a second neurostimulation pattern.

In one implementation of the system, the first neurostimulation pattern and the second neurostimulation pattern differ in one or more parameters selected from a group consisting of waveform pattern, a value of a peak positive stimulus, a value of a peak negative stimulus, total energy per pulse, and average power. The control unit can further excite the tissue with the second neurostimulation pattern, receive a second magnetic signal corresponding to the second neurostimulation pattern from the one or more magnetic sensors, apply the machine learning algorithm to the second neurostimulation pattern and the second magnetic signal to generate a third neurostimulation pattern, forming an active feedback loop.

In one implementation of the system, the control unit can segment the magnetic signals into a first component and a second component, wherein the first component is of a larger magnitude than the second component and extract the second component of the magnetic signal to obtain a signal of interest, wherein machine learning algorithm is applied to the signal of interest.

In one implementation of the system, the system can further include a magnetic shield configured to be implanted around the one or more magnetic sensors for shielding the one or more magnetic sensors from external magnetic fields. Additionally, a wearable magnetic shield can be worn over a body portion.

In one implementation of the system, the first neurostimulation pattern and the second neurostimulation pattern differ in the waveform pattern only.

In one aspect, disclosed is a method of neurostimulation using the disclosed neurostimulation system. The method can include the steps of applying a first neurostimulation pattern to the tissue resulting in an excited tissue; receiving a first magnetic signal corresponding to the first neurostimulation pattern of the excited tissue; and applying a machine learning algorithm to the first neurostimulation pattern and the first magnetic signal to generate a second neurostimulation pattern.

In one implementation of the method, the first neurostimulation pattern and the second neurostimulation pattern differ in waveform pattern but have substantially same amount of energy per pulse. Alternatively, the first neurostimulation pattern and the second neurostimulation pattern differ in one or more parameters selected from a group consisting of waveform pattern, a value of a peak positive stimulus, a value of a peak negative stimulus, total energy per pulse, and average power.

In one implementation of the method, the method can further include the steps of: applying, by the control unit, through the one or more stimulating leads, the second neurostimulation pattern to the tissue; receiving, by the control unit, a second magnetic signal corresponding to the second neurostimulation pattern from the one or more magnetic sensors; and applying the machine learning algorithm to the second neurostimulation pattern and the second magnetic signal to generate a third neurostimulation pattern, resulting in an active feedback loop.

In one implementation of the method, the method can further include the steps of: applying an algorithm to segment the first magnetic signal into a first component and a second components, wherein the second component is of a larger magnitude than the first component; extracting the first component of the first magnetic signal to obtain a signal of interest, wherein machine learning algorithm is applied to the signal of interest.

In one implementation of the method, the method can further include the steps of: implanting the one or more stimulating leads in the tissue; implanting the one or more magnetic sensors near the excited tissue; and implanting the magnetic shield around the one or more magnetic sensors to shield the one or more magnetic sensors from the external magnetic fields. The method may further include the step of wearing an external wearable magnetic shield that can be worn over a body portion.

These and other objects and advantages of the embodiments herein and the summary will become readily apparent from the following detailed description taken in conjunction with the accompanying drawings.

BRIEF DESCRIPTION OF THE DRAWINGS

The accompanying figures, which are incorporated herein, form part of the specification and illustrate embodiments of the present invention. Together with the description, the figures further explain the principles of the present invention and to enable a person skilled in the relevant arts to make and use the invention.

DETAILED DESCRIPTION

Figure 1:
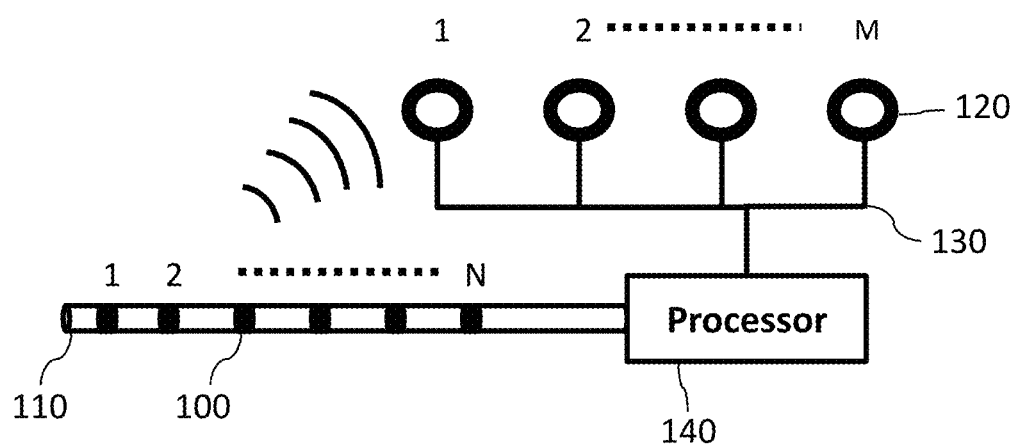
FIG. 1 depicts the system for neurostimulation, according to an exemplary embodiment of the present invention.

Subject matter will now be described more fully hereinafter with reference to the accompanying drawings, which form a part hereof, and which show, by way of illustration, specific exemplary embodiments. Subject matter may, however, be embodied in a variety of different forms and, therefore, covered or claimed subject matter is intended to be construed as not being limited to any exemplary embodiments set forth herein; exemplary embodiments are provided merely to be illustrative. Likewise, a reasonably broad scope for claimed or covered subject matter is intended. Among other things, for example, the subject matter may be embodied as methods, devices, components, or systems. The following detailed description is, therefore, not intended to be taken in a limiting sense.

The word "exemplary" is used herein to mean "serving as an example, instance, or illustration." Any embodiment described herein as "exemplary" is not necessarily to be construed as preferred or advantageous over other embodiments. Likewise, the term "embodiments of the present invention" does not require that all embodiments of the invention include the discussed feature, advantage, or mode of operation.

The terminology used herein is for the purpose of describing particular embodiments only and is not intended to be limiting of embodiments of the invention. As used herein, the singular forms "a", "an" and "the" are intended to include the plural forms as well, unless the context clearly indicates otherwise. It will be further understood that the terms "comprise", "comprising,", "includes" and/or "including", when used herein, specify the presence of stated features, integers, steps, operations, elements, and/or components, but do not preclude the presence or addition of one or more other features, integers, steps, operations, elements, components, and/or groups thereof.

The following detailed description includes the best currently contemplated mode or modes of carrying out exemplary embodiments of the invention. The description is not to be taken in a limiting sense but is made merely for the purpose of illustrating the general principles of the invention, since the scope of the invention will be best defined by the allowed claims of any resulting patent.

Disclosed is a system and method for neurostimulation that can modify the electrical pulses based on feedback from the stimulated neural tissues. The disclosed system is based on an approach to adapting the parameters of the electrical stimulus to the environment in which the stimulus is being applied. When ionic current passes through excited tissues, they produce a magnetic field, wherein the strength of the magnetic field can be proportional to the intensity of the ionic currents. In other words, the magnetic field generated can be proportional to the end-effect (the action potential that propagates in the tissue). The generated magnetic field can provide feedback for applied electrical neurostimulation. The disclosed system based on the feedback can modify the electrical neurostimulation pattern till an optimum neurostimulation pattern can be achieved. The feedback can be received continuously by the disclosed system or can be received as and when desired to reprogram the system with the optimum neurostimulation pattern.

Referring to FIG. 1, which discloses an exemplary embodiment of the disclosed system and method for magnetic feedback-based neurostimulation. The system can include a number of stimulating electrodes 100 (1 to N) mounted on a flexible lead 110, a number of magnetic sensors 120 (1 to M), connected through a sensor harness 130 to the processor 140. The function of the stimulating electrodes is to establish an interface with tissues so that nerves are electrically stimulated to achieve the desired neuromodulation effect. For example, this neuromodulation effect can be to block pain signals, preventing these signals to reach the corresponding brain area hence relieving the patient of the feeling of pain.

The function of the magnetic sensors 120 can be to probe the waveform of the magnetic field generated from the passage of ionic currents in the excited tissues in response to the neurostimulation. This information can be used by the processor to generate the optimum neurostimulation pattern including the waveform and energy per pulse delivered through the stimulating electrodes. As such, the magnetic sensors transform the magnetic field created from the passage of ionic currents in the excited tissues into a signal of interest readable by the processor. The adjustment of the electrical stimuli by the processor includes but is not limited to the determination of a specific waveform, the value of the peak positive stimulus, peak negative stimulus, the total energy per pulse, and average power. Such determination is based on the signals recorded by the magnetic sensors.

The magnetic sensors transduce a magnetic field into an electrical signal. One typical type of magnetic sensor can be a coil which can perform this function based on Faraday's law. There are many other types of magnetic sensors known to a skilled person for transforming the magnetic field to a signal of interest, and any such magnetic sensor is within the scope of the present invention. In one case, for very low amplitude magnetic fields, a SQUID (Superconducting Quantum Interference Device) can be used, with established applications such as recording magneto-encephalograms (MEG).

The processor can deliver stimulus in a predetermined neurostimulation pattern to the target tissues via the stimulating electrodes. The stimulus can be in the form of pulses of electrical voltage or current in a predetermined pattern. The stimulating electrodes can be provided on the flexible lead, referred hereinafter to as lead electrodes. Each electrode can be in any of the following three states: active (electrically positive), reference (electrically negative), or neutral (electrically float or not electrically connected). Setting an electrode in the active, reference, or neutral modes allows for spatially shaping the paths of electrical currents in the tissues so that the desired neuromodulation effect (such as pain relief) can be optimized.

In one exemplary embodiment, the magnetic sensors can be installed at locations so as they can pick up signals with maximum strength from the tissues of interest. Thus, the sensors can be placed far away from the stimulus point, close to the area where the net effect of the excitation is intended. One way to ascertain the correctness of the location could be during implantation, by checking the strength of the signals based on the actual configuration. As the sensors could move during operation, a multiplicity of sensors can provide some redundancy. Moreover, multiple sensors can be arranged to pick up a certain area of interest.

In general, the stimulation of tissues with electrical pulses can generate two magnetic field components. One component of this magnetic field is directly due to the stimulation itself and can be eliminated. The first component can be expected to be of a very large amplitude but can be easily eliminated by time gating or other techniques. The 2nd component can be due to the action potential generated in the tissues of interest as a result of the electrical pulse, which can be the signal of interest. This component can be of very small amplitude. Although both components have some information (for example the 1st component could be used to ascertain the health of the electrical stimulation itself), it is only the second component that carries the useful information with respect to achieving the stimulation of targeted tissues. This second component of the magnetic field can be used so that the magnitude and shape of the electrical impulse waveforms can be adjusted to achieve the desired effect (effective stimulation of the tissues of interest). The system can store the optimized magnitude and shape of the electrical impulses as the neurostimulation pattern. However, the neurostimulation pattern can be optimized as and when required. Alternatively, an active feedback loop can be formed and the neurostimulation can be optimized in near real-time.

Figure 2:
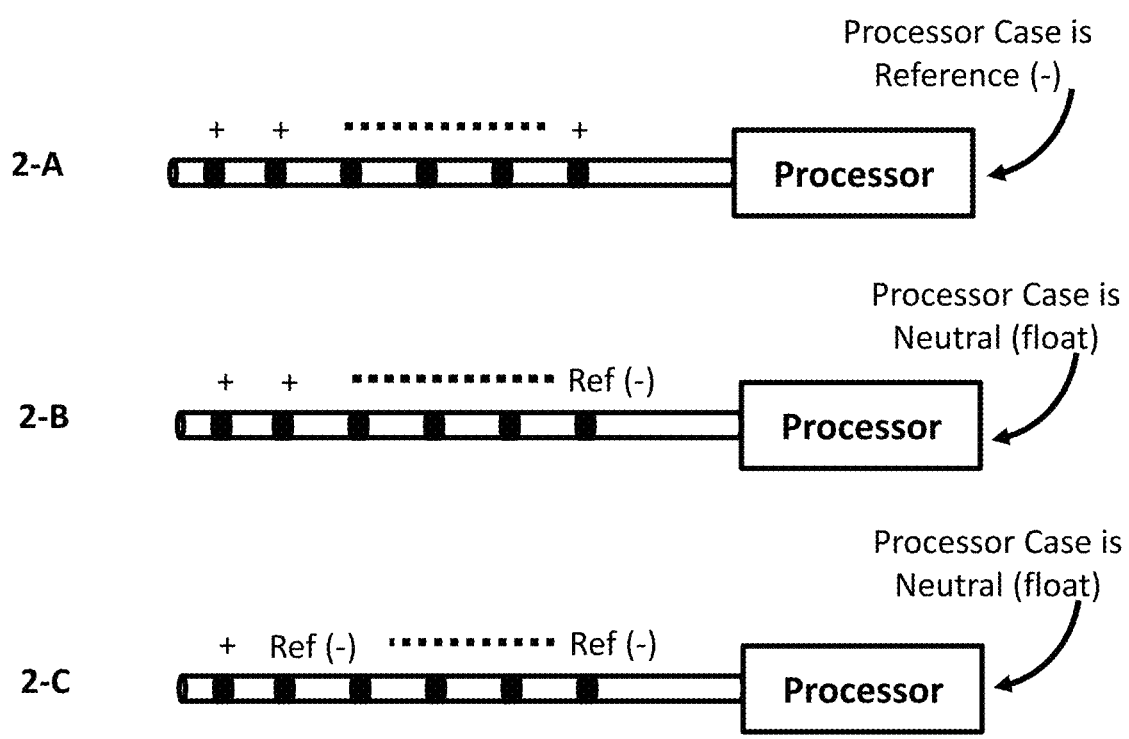
FIG. 2 depicts some possible stimulation electrode configurations, according to an exemplary embodiment of the present invention.
Figure 3:
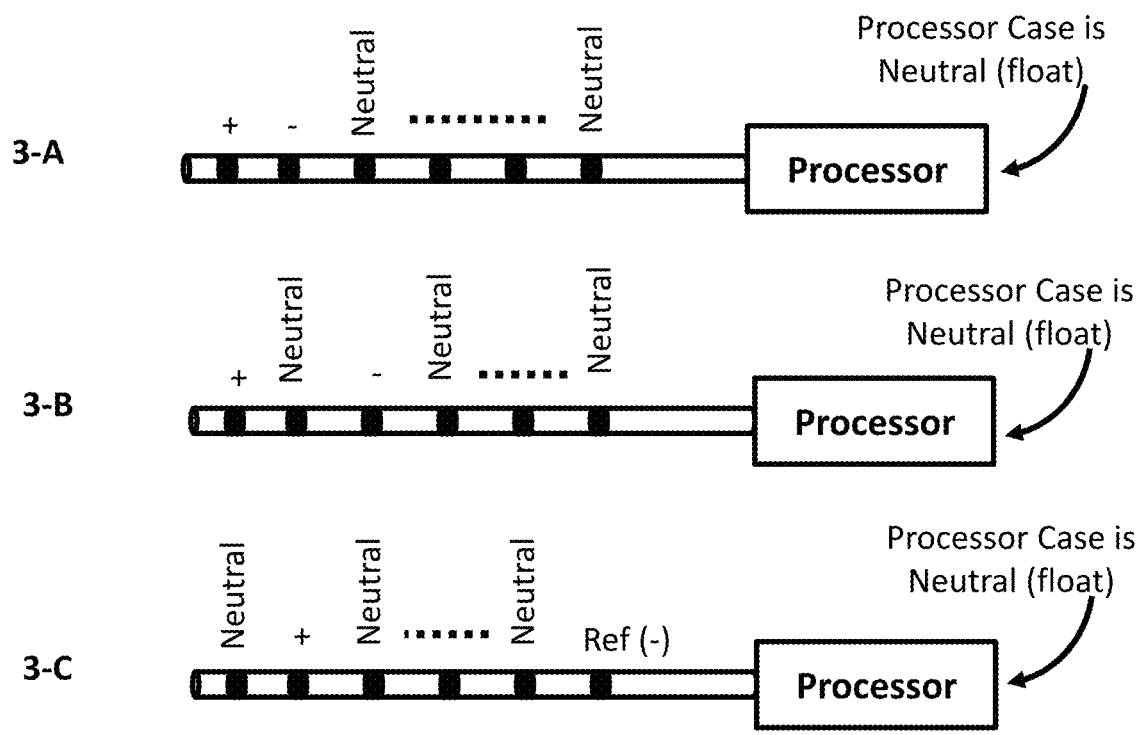
FIG. 3 depicts additional stimulation electrode configurations, according to an exemplary embodiment of the present invention.

Referring to FIG. 2 which illustrates the determination of the reference (negative pole) electrode(s) and active (positive pole) electrode(s). The reference electrode in 2A is the case of the processor, whereas all other lead electrodes are active. The reference electrode in 2B is one of the lead electrodes located on the flexible lead whereas all other lead electrodes are active. In this case, the case of the processor will not be electrically active (float state with respect to electrical voltage/current). In 2C, a group of electrodes is internally connected to form the reference electrode, whereas only one electrode is active, with the case remaining neutral. For the sake of clarity, abstraction is made of the other elements forming the stimulator. Referring to FIG. 3 which shows more possible combinations for the electrode configurations. 3A shows only 2 lead electrodes participate in the stimulus whereas all other electrodes are float. In 3B and 3C, only 2 lead electrodes participate in the stimulus whereas all other electrodes are float. The 2 participating electrodes are separated by a greater distance. The selection of electrodes participating in the electrical stimulation and remaining neutral allows for a granular spatial shaping of the distribution of current flow in the tissues and is also part of the adjustment that can be made based on the feedback recorded from the magnetic field generated by the stimulus. For the sake of clarity, abstraction is made of other possible combinations and other elements forming the stimulator.

Figure 4A:
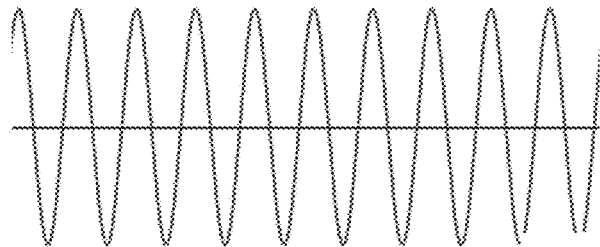
FIG. 4A depicts exemplary excitation waveforms, according to an exemplary embodiment of the present invention.
Figure 4A:
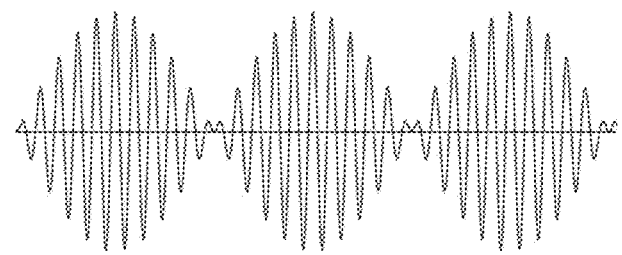
Figure 4A:
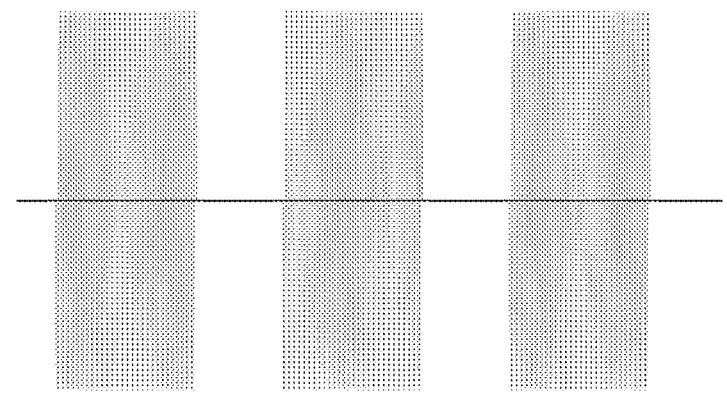
Figure 4A:
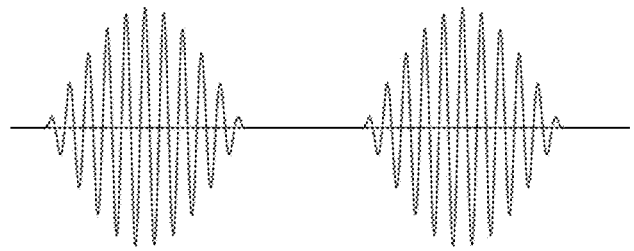
Figure 4B:
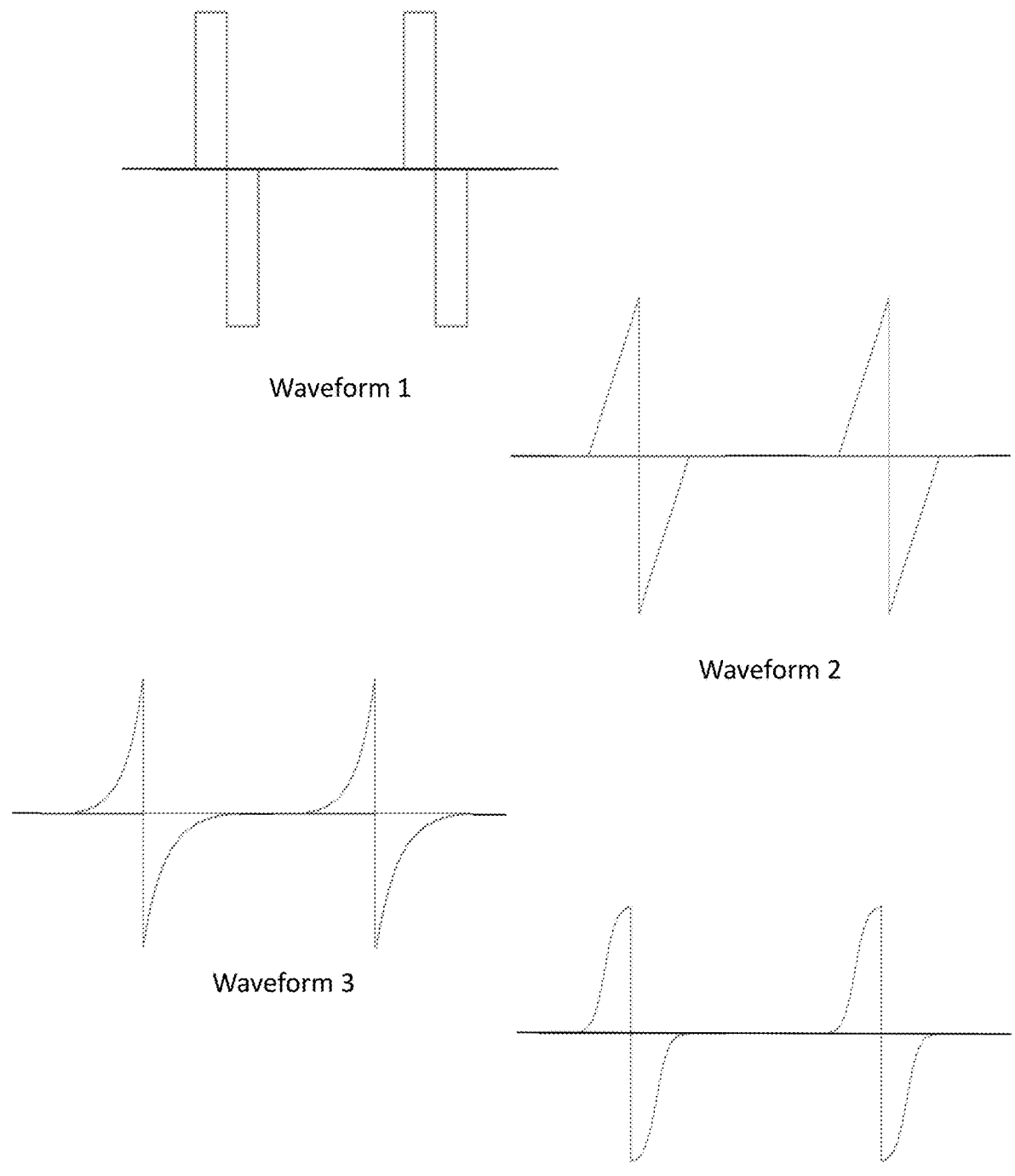
FIG. 4B depicts additional exemplary excitation waveforms, according to an exemplary embodiment of the present invention.
Figure 4C:
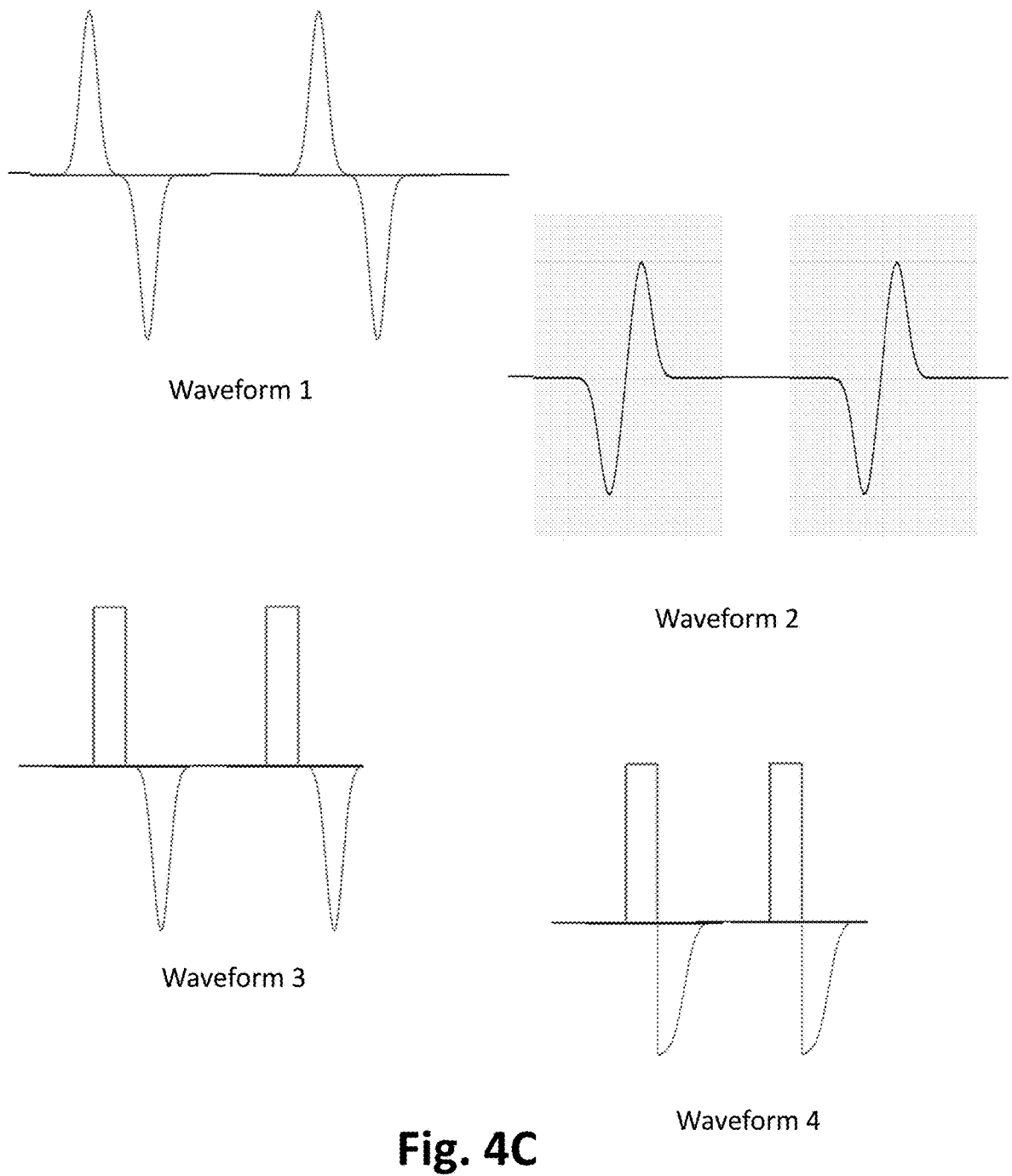
FIG. 4C depicts additional exemplary excitation waveforms, according to an exemplary embodiment of the present invention.

Referring to FIGS. 4A-4C, which illustrates samples of possible waveforms of electrical stimulation by the electrodes. These waveforms can be monopolar/bipolar square, triangular, sawtooth, sinusoidal, sigmoidal, or any arbitrary shape. The envelope of the stimulus signal, also controlled by the processor, can be increased, or decreased over time to create the desired neuromodulating effect. The rate of increase can be linear, exponential, or any other arbitrary shape. This repetition rate (firing rate) of the pulses is a stimulation parameter controlled by the Processor. This repetition rate can be constant or pseudo-random.

Figure 5:
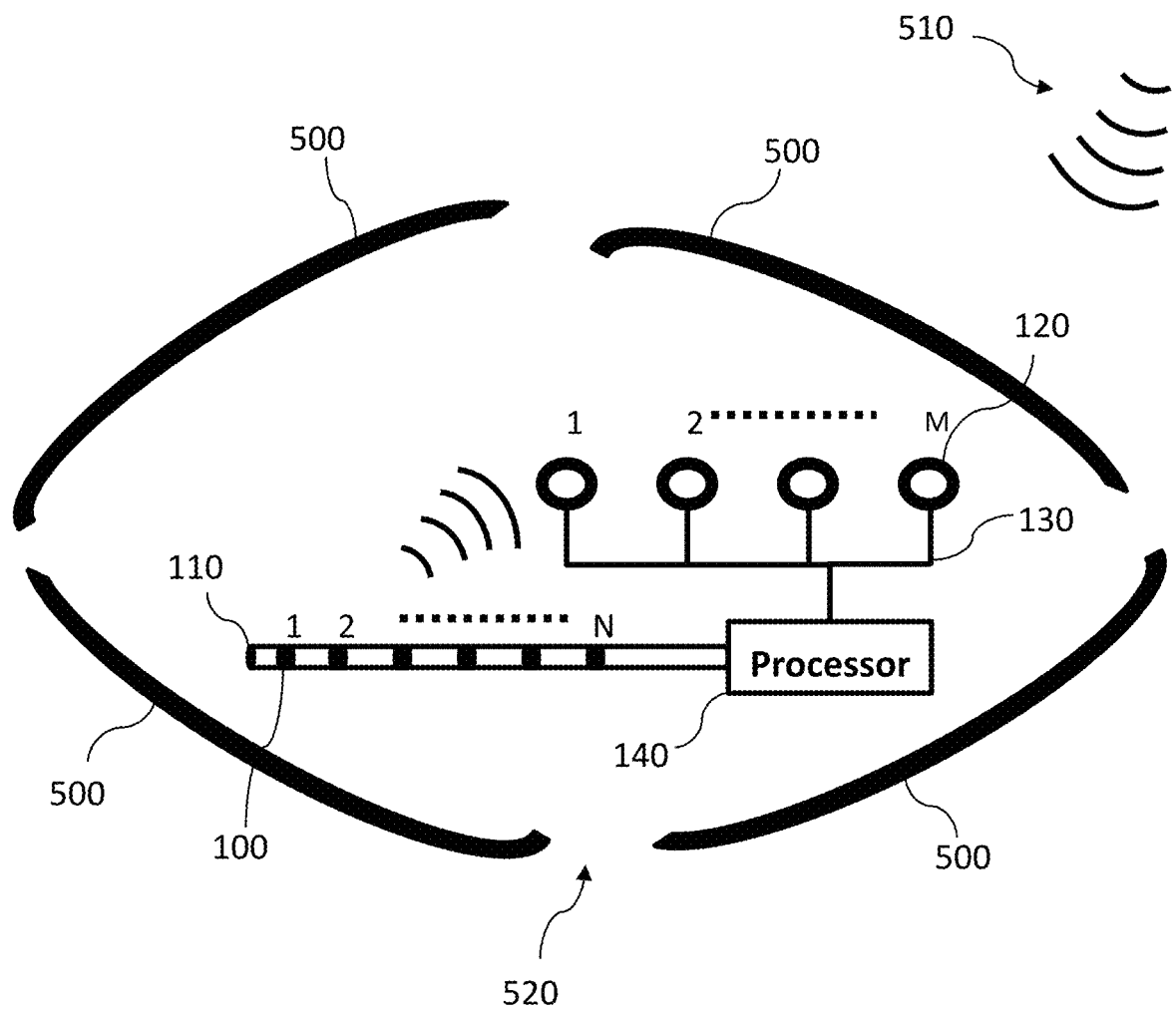
FIG. 5 depicts the magnetic shielding of the magnetic sensors, according to an exemplary embodiment of the present invention.

Referring to FIG. 5, the magnetic sensors 120 can also be exposed to external magnetic fields 510 generated by sources unrelated to the electrical stimulation created by the neurostimulator. These external fields can also be captured to a different extent by each of the magnetic sensors, depending on their location and direction. The magnetic sensors can be shielded from external magnetic fields by using magnetic shields 500. The magnetic shields 500 can be installed in the body while implanting the electrodes, also referred herein as the internal magnetic shields. The internal magnetic shield 500 can be used to prevent the magnetic sensors 120 from being saturated by the potentially high-intensity magnetic fields generated by external sources. The magnetic shields 500 can be implanted during surgery in such a way as to mitigate the interference caused by external magnetic sources. In one case, a signal processing algorithm based on the correlation between the stimulus pattern and the magnetic fields recorded by the sensors can be used for the elimination of any residual effects of external magnetic fields from the signal captured by the magnetic sensors.

The frequency spectrum of the magnetic fields generated by the action potentials in the tissues can be generally low. For example, frequencies below 10 kHz can be generally observed. Suitable material of magnetic shield can be selected based on this. However, due to the proliferation of many high-frequency sources such as 5G cellular frequency bands, magnetic shields can be used. In one case, the polymer shields can be a good choice, as they can be made flexible hence follow the contour of the human body. In one exemplary embodiment, the processor by the mean of signal processing algorithms can isolate the signal of interest from the interferences. Separate magnetic sensors can be used to record the waveform of the external magnetic field, and the input from the main magnetic sensor can be filtered by the processor to remove the interferences from the external magnetic field and isolate the signals of interest. Machine learning models can be used to isolate the signal of interest and remove the interferences caused by an external magnetic field. The machine learning model can be trained with training datasets having signal information samples from external magnetic fields and signals of interest. Alternatively, a suitable algorithm can be programmed to filter the interferences.

It is to be understood that the 3-D shape of the magnetic shield, represented in 2-D in FIG. 5, is deliberately irregular as it must satisfy the space requirements of the implant. Moreover, openings 520 in the shield allow for the passage of tissues that cannot be moved nor cut during the implant surgery to insert the shield, such as nerves or veins and arteries. The magnetic shield redirects the magnetic lines of flux around the shield. The magnetic shield can be made from biocompatible ferromagnetic material with high magnetic permeability. The thickness of the shield can be determined on a case-by-case basis depending on the environment where the patient usually resides in. The higher the strength of the external magnetic field, the thicker the shield will be so that the magnetic flux lines can be adequately diverted.

Figure 6A:
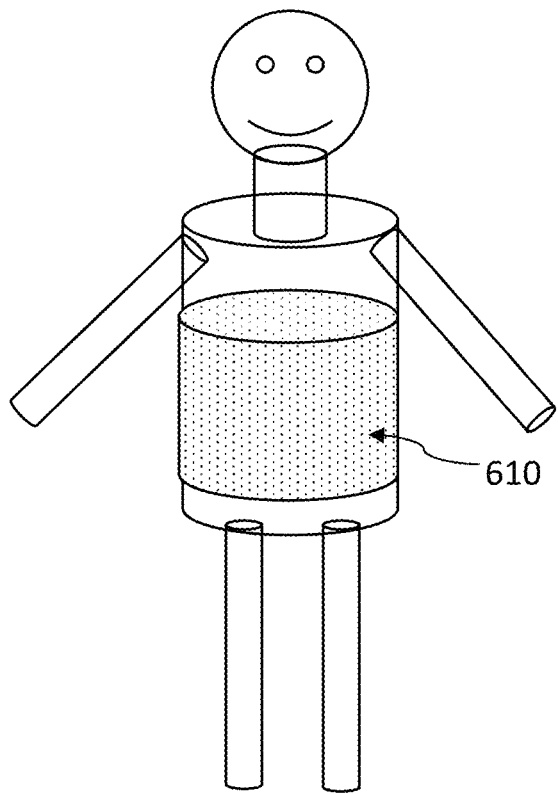
FIG. 6A depicts a partial wearable magnetic shield, according to an exemplary embodiment of the present invention.
Figure 6B:
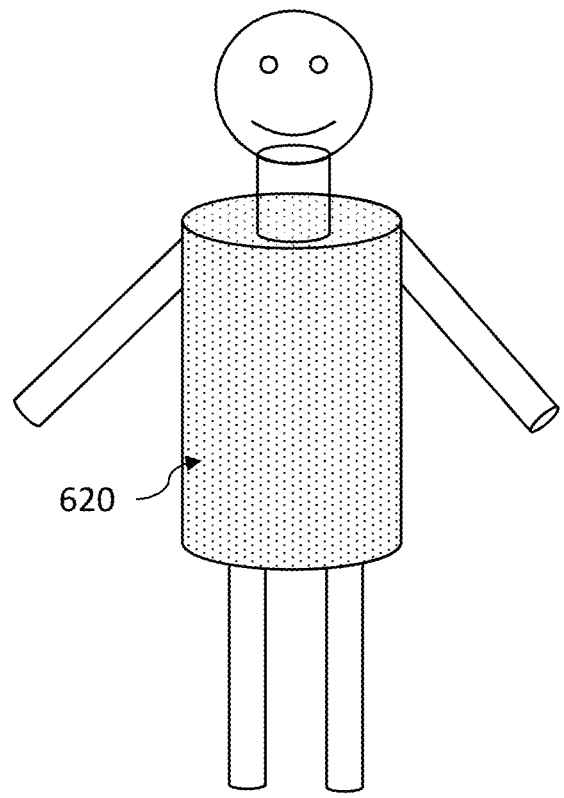
FIG. 6B depicts a full wearable magnetic shield, according to an exemplary embodiment of the present invention.

Besides the internal implantable magnetic shield, provision can be made for an external magnetic shield in the form of a wearable shield. This shield will be affixed around the patient's trunk as an undergarment concealing its presence. For example, FIG. 6A shows a partial shield that offers the convenience of easy wearing, whereas FIG. 6B depicts a more comprehensive shield that will be more effective but at the cost of less convenient usage for the patient. In one case, the combination of the internal and external magnetic shields ensures a comfortable setting whereas either the external shield is sufficient, or that a thin internal shield is deemed sufficient when the patient is subject to low-intensity magnetic fields. When exposed to high magnetic fields, the patient can use the external wearable shield, irrespective of having internal magnetic shields being implanted.

Figure 7:
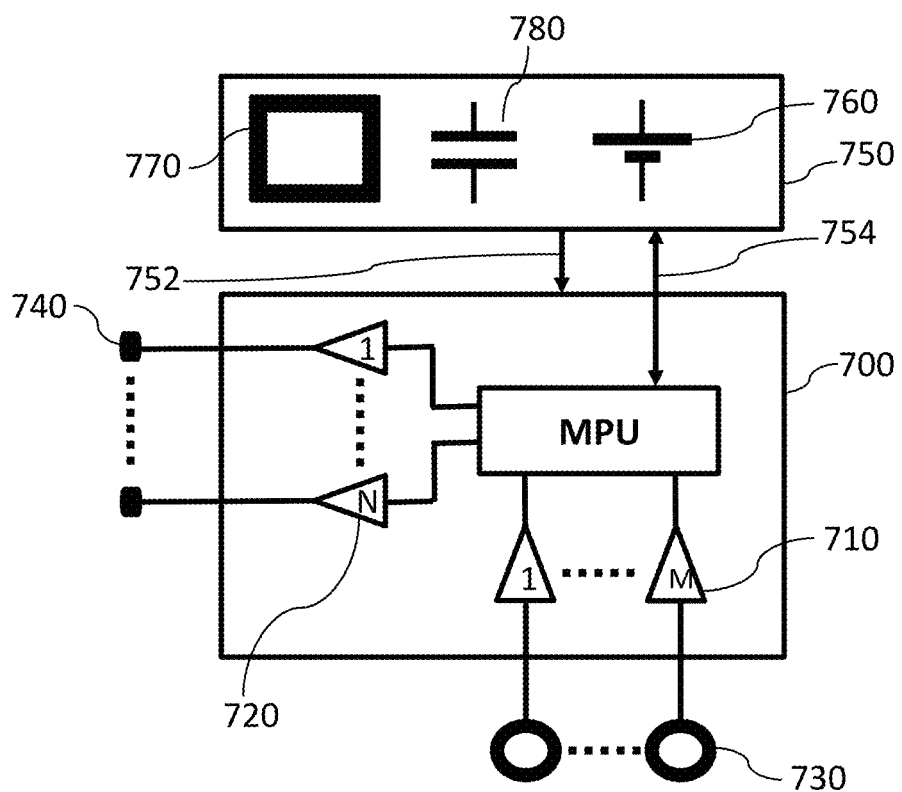
FIG. 7 is a circuit diagram of the system for neurostimulation having the processor and the wireless power/data module, according to an exemplary embodiment of the present invention.

The source of power for the disclosed system can be an internal stand-alone battery, a rechargeable battery charged through a wireless power transmission device, or completely using a battery-less a wireless power transmission device. The wireless power transmission device can use ultrasound or radio-frequency waves to transfer power to the implanted device. FIG. 7 illustrates an embodiment of the system where the processor and the wireless power/data module are represented.

Referring to FIG. 7 which shows the processor 700 that can include sense amplifiers 710 and signal conditioning amplifiers 720. The magnetic sensors 730 can be operably connected to the processor 700 via the sense amplifiers. The stimulating leads 740 can be connected to the processor 700 via the signal conditioning amplifiers 720. The wireless power/data module 750 can be seen coupled to the processor 700 through data line 754 and a power line 752. The embedded antenna 770 in the wireless power/data module 750 can wirelessly transmit energy from outside of the patient body into electrical energy. This electrical energy can include two components: power and data. The power component of the energy can be transferred via internal circuitry (not shown) to energy storage elements. The energy storage elements consist of a capacitor 780 and/or a battery 760. The advantage of only using a capacitor instead of a battery is to prevent any adverse effect that may occur due to leaking of the battery's chemical materials into the body of the patient. In case a battery is used, the wireless power transfer ensures that this battery stays always charged, therefore significantly extending battery life with the advantage of not needing any replacement.

The Processor can be powered by the Power Line from the Wireless Power/Data Module. The data component of the wirelessly transmitted energy can be transferred to the Processor via the Data Line of the Wireless Power/Data Module. This data line can be bidirectional and carries programming instructions from the outside to the implant during programming mode. The Processor can transmit internal status information to the outside world via the Wireless Data/Power Module and using the same Data Line.

The Processor can consist of the Main Processing Unit (MPU), M Sense Amplifiers, and N Signal Conditioning Amplifiers. Each of the M Sense Amplifiers can be connected to a Magnetic Sensor exposed to the magnetic fields generated by the passage of current in the tissues (wanted signals) as well as a residual magnetic field from external sources (unwanted signals). Each of the N Signal Conditioning Amplifiers can be connected to a Stimulating Electrode delivering electrical energy to the target tissues to achieve the desired effect. The Main Processing Unit can control the type of electrical stimulus to be delivered to each of the N Stimulating Electrodes using various signal and data processing algorithms including but not limited to Adaptive Filtering, Cross-Correlation analysis, Artificial Intelligence-assisted closed-loop control. This closed-loop control mechanism can ensure that the best matching occurs between the electrical circuitry and target tissues. In one case, the waveform, maximum and minimum values, energy per pulse, average power, and other stimulus parameters of the disclosed system can be controlled by the processor using an algorithm to process signals recorded by magnetic sensors.

Figure 8:
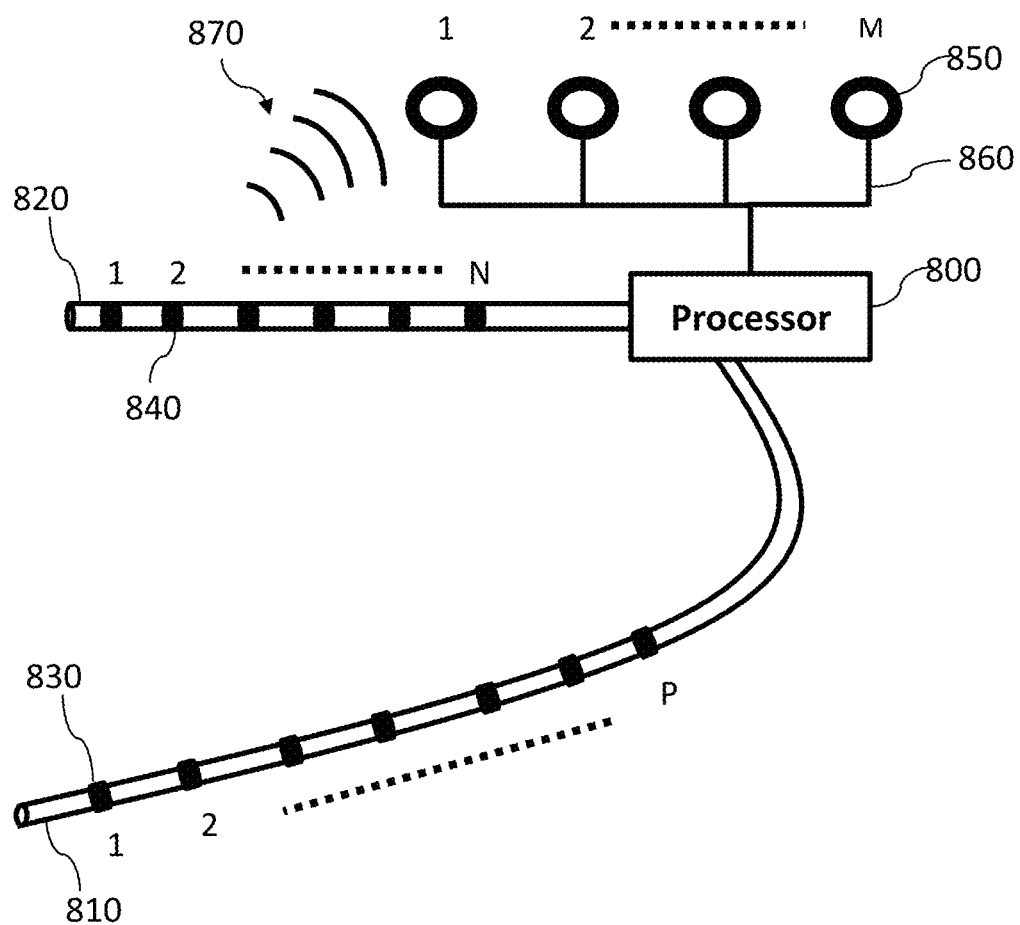
FIG. 8 depicts a dual-lead system, according to an exemplary embodiment of the present invention.

Referring to FIG. 8 which shows an extension of the single lead system depicted in FIG. 1 to a dual-lead system. Both leads 810 and 820 can be flexible, wherein the lead 810 can include stimulating electrodes 830 and the lead 820 can include stimulating electrodes 840. The number of stimulating electrodes on each lead can be different, for example, the stimulating electrodes can be 1 to N for the first lead and 1 to P for the second lead. The determination of the mode of operation for each electrode (active, reference, and neutral), as well as all stimulation parameters of each electrode, can be determined by the processor to optimize the stimulation pattern to achieve the desired effect. Any electrode from one lead can act as the neutral, active, or reference for any other electrode for the other lead. This feature can allow for better spatial distribution and focus of the stimulation currents in the target tissues. It is be understood that without any loss in generality, the dual-lead system can be extended to any number of extra leads, without departing from the scope of the present invention. FIG. 8 also shows the processor 800 electrically coupled to the magnetic sensor 850 through the harness 860. FIG. 8 also shows the magnetic field 870 produced by the passage of ionic currents in the excited tissue, the strength of magnetic field 870 can be measured by the magnetic sensors 850.

Figure 9:
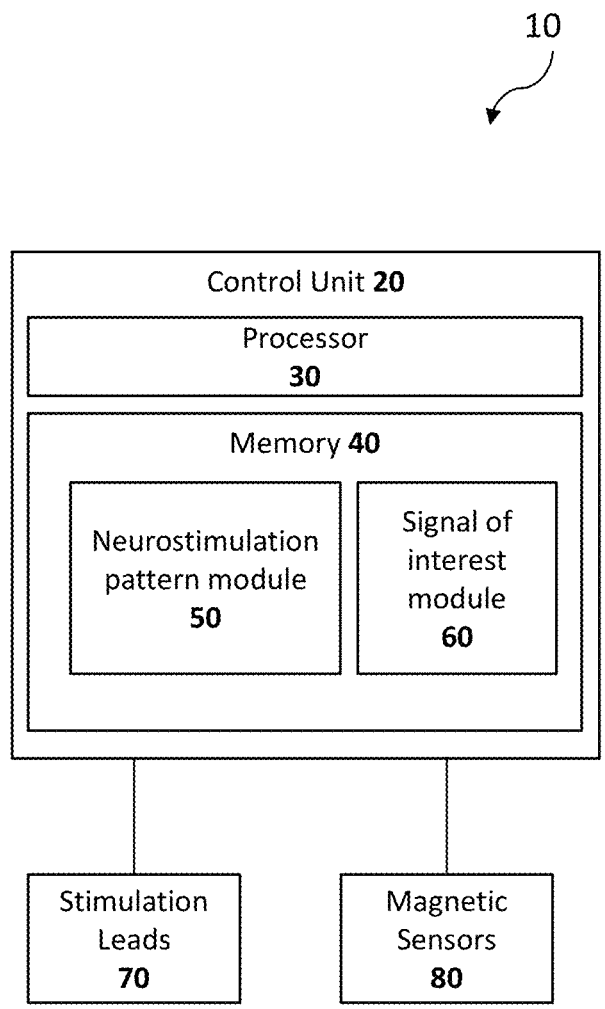
FIG. 9 is a block diagram showing an exemplary embodiment of the system, according to the present invention.

Referring to FIG. 9 which is a block diagram of the disclosed system 10 having a control unit 20 connected to stimulation leads 70 and magnetic sensors 80. The control unit can include a processor 30 and a memory 40, wherein the memory 40 can be operably coupled to the processor, for example by a system bus. It is to be understood that FIG. 9 shows a single processor, however, more than one processor is within the scope of the present invention. Moreover, a processor generating electrical pulses and/or current/voltage can be different from a processor that can define the neurostimulation pattern based on feedback from the magnetic sensors. For example, the neurostimulation pattern can be generated by one processor and downloaded to another processor connected to the stimulating leads for generating the electrical pulses and/or current/voltage. The neurostimulation pattern can include information related to electrical pulses and current/voltage including specific waveform or waveform shape/pattern, the value of the peak positive stimulus, the value of peak negative stimulus, the total energy per pulse, and average power.

Memory 40 can include a neurostimulation pattern module 50 and signal of interest module 60. The signal of interest module 60 can receive signals from the magnetic sensors. Such signals can include interferences from the external magnetic fields and any other noise. The signal of interest module 60 can extract signals of interest by processing the dual-component magnetic signal received from the magnetic sensors and filter the interferences, hence extracting the desired component. The signal of interest module 60 can include machine learning models trained using a training dataset containing magnetic signals from sensors, external magnetic field information, and general noises in the signal of interest. The extracted signal of interest can be processed by the neurostimulation pattern module 50. The neurostimulation pattern module 50 can include machine learning-based algorithms that can take the signal of interest and the neurostimulation pattern in response to which the signal of interest is obtained as the inputs, referred to as the first neurostimulation pattern. The machine learning algorithms can be applied to modify the first neurostimulation pattern to the second neurostimulation pattern. Similarly, the feedback of the second neurostimulation pattern can be observed by the control unit and the second neurostimulation pattern can be further modified and the steps can be repeated till the desired neurostimulation pattern can be achieved. The pre-trained machine learning models can further learn from the feedback to generate the desired neurostimulation pattern specific for a patient.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above-described embodiment, method, and examples, but by all embodiments and methods within the scope and spirit of the invention as claimed.

What is claimed is:

1. A system for neurostimulation, the system comprising:
one or more stimulating electrodes configured to transmit a neurostimulation pattern to a tissue, wherein the neurostimulation pattern comprises waveform and energy per pulse;

a control unit operably coupled to the one or more stimulating electrodes; and one or more magnetic sensors operably coupled to the control unit and configured to sense magnetic fields generated by action potentials in the tissue being excited by the neurostimulation pattern and generate a magnetic signal in response to the sensed magnetic fields, wherein the control unit is configured to:
generate a signal of interest from the magnetic signal;
transmit a first neurostimulation pattern to the tissue for exiting the tissue with the first neurostimulation pattern,
generate, from a first magnetic signal received from the one or more magnetic sensors, a first signal of interest corresponding to the first neurostimulation pattern, and
generate a second neurostimulation pattern based on the first neurostimulation pattern and the first signal of interest, wherein the second neurostimulation pattern is different from the first neurostimulation pattern.

2. The system according to claim 1, wherein the first neurostimulation pattern and the second neurostimulation pattern differ in one or more parameters selected from a group consisting of waveform pattern, total energy per pulse, and average power.

3. The system according to claim 2, wherein the first neurostimulation pattern and the second neurostimulation pattern differ in the waveform pattern only.

4. The system according to claim 1, wherein the control unit is further configured to:
transmit the second neurostimulation pattern to the tissue for exciting the tissue with the second neurostimulation pattern;
generate, from a second magnetic signal received from the one or more magnetic sensors, a second signal of interest corresponding to the second neurostimulation pattern,
generate a third neurostimulation pattern based on the second neurostimulation pattern and the second signal of interest.

5. The system according to claim 1, wherein the control unit is further configured to:
segment the magnetic signal into a first component and a second component, wherein the second component is of a lesser magnitude than the first component;
extract the second component of the magnetic signal to generate the signal of interest.

6. The system according to claim 1, wherein the system further comprises an internal magnetic shield configured to be spatially positioned around the one or more magnetic sensors for shielding the one or more magnetic sensors from an external magnetic field.

7. The system according to claim 6, wherein the system further comprises a wearable magnetic shield that can be worn over a body portion.

8. A method of neurostimulation, the method comprising the steps of:
providing a neurostimulation system comprising:
one or more stimulating electrodes configured to transmit a neurostimulation pattern to a tissue, wherein the neurostimulation pattern comprises waveform and energy per pulse,
a control unit operably coupled to the one or more stimulating electrodes, and
one or more magnetic sensors operably coupled to the control unit and configured to sense magnetic fields generated by action potentials in the tissue being excited by the neurostimulation pattern, and generate a magnetic signal in response to the sensed magnetic fields
wherein the control unit is configured to generate a signal of interest from the magnetic signal;
applying, by the control unit, through the one or more stimulating electrodes, a first neurostimulation pattern to the tissue for exciting the tissue with the first neurostimulation pattern;
generating, by the control unit, from a first magnetic signal received from the one or more magnetic sensors, a first signal of interest corresponding to the first neurostimulation pattern; and
generating, by the control unit, a second neurostimulation pattern based on the first neurostimulation pattern and the first signal of interest, wherein the second neurostimulation pattern is different from the first neurostimulation pattern.

9. The method according to claim 8, wherein the first neurostimulation pattern and the second neurostimulation pattern differ in waveform pattern but have similar amount of energy per pulse.

10. The method according to claim 8, wherein the first neurostimulation pattern and the second neurostimulation pattern differ in one or more parameters selected from a group consisting of waveform pattern, total energy per pulse, and average power.

11. The method according to claim 8, wherein the method further comprises:
applying, by the control unit, through the one or more stimulating electrodes, the second neurostimulation pattern to the tissue for exciting the tissue with the second neurostimulation pattern;
generating, by the control unit, from a second magnetic signal received from the one or more magnetic sensors, a second signal of interest corresponding to the second neurostimulation pattern; and
generating a third neurostimulation pattern based on the second neurostimulation pattern and the second signal of interest, wherein the third neurostimulation pattern is different from the second neurostimulation pattern.

12. The method according to claim 8, wherein the method further comprises:
segmenting the magnetic signal into a first component and a second component, wherein the second component is of a larger magnitude than the first component;
extracting the first component of the magnetic signal to generate the signal of interest.

13. The method according to claim 8, wherein the neurostimulation system further comprises:
an internal magnetic shield configured to be spatially positioned around the one or more magnetic sensors for shielding the one or more magnetic sensors from an external magnetic field.

14. The method according to claim 13, wherein the method further comprises:
implanting the one or more stimulating electrodes in the tissue;
implanting the one or more magnetic sensors near the tissue; and
implanting the internal magnetic shield around the one or more magnetic sensors to shield the one or more magnetic sensors from the external magnetic field.

15. The method according to claim 13, wherein the neurostimulation system further comprises a wearable magnetic shield that can be worn over a body portion.

\* \* \* \* \*